US010336693B2

(12) United States Patent
Jung et al.

(10) Patent No.: US 10,336,693 B2
(45) Date of Patent: Jul. 2, 2019

(54) ANTIVIRAL-AGENT RESISTANT VIRUS DETECTION SYSTEM (71) Applicant: KOREA RESEARCH INSTITUTE OF BIOSCIENCE AND BIOTECHNOLOGY, Yuseong-gu Daejeon (KR)

(72) Inventors: Juyeon Jung, Yuseong-gu Daejeon (KR); Eun Kyung Lim, Yuseong-gu Daejeon (KR)

(73) Assignee: Korea Research Institute of Bioscience and Biotechnology, Yuseong-gu, Daejeon (KR)

( * ) Notice: Subject to any disclaimer, the term of this patent is extended or adjusted under 35 U.S.C. 154(b) by 0 days.

(21) Appl. No.: 15/741,577

(22) PCT Filed: Jul. 4, 2016

(86) PCT No.: PCT/KR2016/007191
§ 371 (c)(1),
(2) Date: Aug. 9, 2018

(87) PCT Pub. No.: WO2017/007204
PCT Pub. Date: Jan. 12, 2017

(65) Prior Publication Data
US 2018/0346417 A1 Dec. 6, 2018

(30) Foreign Application Priority Data

Jul. 3, 2015 (KR) .................... 10-2015-0095144

(51) Int. Cl.
*A61K 31/215* (2006.01)
*C07C 323/52* (2006.01)
(Continued)

(52) U.S. Cl.
CPC ............ *C07C 323/52* (2013.01); *A61P 31/16* (2018.01); *C07C 233/52* (2013.01);
(Continued)

(58) Field of Classification Search
CPC ............ G01N 2333/11; G01N 33/553; G01N 33/56983; C07C 323/52; C07C 233/52; A61K 31/215; A61P 31/16
(Continued)

(56) References Cited

FOREIGN PATENT DOCUMENTS

KR 1020110086963 A 8/2011
KR 1020110114981 A 10/2011
(Continued)

OTHER PUBLICATIONS

D'Souza, Charlotte et al., "Search for novel neuraminidase inhibitors: Design, synthesis and interaction of oseltamivir derivatives with model membrane using docking, NMR and DSC methods", Biochimica et Biophysica Acta, May 3, 2009, pp. 1740-1751, vol. 1788, Copyright Elsevier B.V. (2009).
(Continued)

*Primary Examiner* — Taylor V Oh
(74) *Attorney, Agent, or Firm* — Avery N. Goldstein; Blue Filament Law PLLC (57) ABSTRACT An oseltamivir analog and nanoparticles having the analog bound thereto, of the present invention, strongly bind to oseltamivir-resistant influenza virus, and thus, the use of the same can allow detection of oseltamivir-resistant influenza viruses quickly and conveniently with the naked eye. Therefore, the present invention can be favorably utilized in promptly establishing a therapeutic schedule for a patient infected with influenza viruses.

8 Claims, 5 Drawing Sheets (51) Int. Cl.
*C07C 233/52* (2006.01)
*G01N 33/553* (2006.01)
*G01N 33/569* (2006.01)
*C07C 323/12* (2006.01)
*A61P 31/16* (2006.01)

(52) U.S. Cl.
CPC ......... *C07C 323/12* (2013.01); *G01N 33/553* (2013.01); *G01N 33/56983* (2013.01); *C07B 2200/07* (2013.01); *C07C 2601/16* (2017.05); *G01N 2333/11* (2013.01)

(58) Field of Classification Search
USPC ........................................................ 514/529
See application file for complete search history.

(56) References Cited

FOREIGN PATENT DOCUMENTS

| KR | 1020120122385 A | 11/2012 |
|---|---|---|
| KR | 1020130022896 A | 3/2013 |
| KR | 1020130085950 A | 7/2013 |

OTHER PUBLICATIONS

Stanley, Mathew et al., "TamiGold': phospha-oseltamivir-stabilised gold nanoparticles as the basis for influenza therapeutics and diagnostics targeting the neuraminidase (instead of the hemagglutinin)", Med. Chem. Commun. (2012), pp. 1373-1376, vol. 3, Copyright The Royal Society of Chemistry (2012); DOI: 10.1039/c2md20034a.

Marin, Maria J. et al., "Glyconanoparticles for the plasmonic detection and discrimination between human and avian influenza virus", Organic & Biomolecular Chemistry (2013), pp. 7101-7107, vol. 11, Copyright The Royal Society of Chemistry (2013); DOI: 10.1039/c3ob41703d.

Hong, Bei-Tao et al., "Oseltamivir hydroxamate and acyl sulfonamide derivatives as influenza neuraminidase inhibitors", Bioorganic & Medicinal Chemistry, Oct. 25, 2014, pp. 6647-6654, vol. 22, Copyright Elsevier Ltd. (2014).

International Search Report dated Oct. 6, 2016 for International Application No. PCT/KR2016/007191 filed Jul. 4, 2016.

ANTIVIRAL-AGENT RESISTANT VIRUS DETECTION SYSTEM

TECHNICAL FIELD

The present invention relates to a system for detecting antiviral agent-resistant virus.

BACKGROUND ART

Influenza is a respiratory disease that spreads through the respiratory system of people and animals (birds, pigs, dogs, horses, etc.) by the influenza virus. Human influenza occurs in the 10-20% of the world population annually and becomes epidemic every year worldwide due to its high contagiousness. Symptoms of influenza include high fever, headache, muscle aches, inflammation of the throat, pain, respiratory diseases such as cough, etc. In severe cases, influenza can cause death in elderly people, people with chronic diseases, and the like.

If influenza infection is suspected, it should be promptly treated to prevent dangerous situations and prevent influenza from spreading to other people. Currently, oseltamivir phosphate (Tamiflu) is mainly used for the treatment of influenza infection, and virus mutants showing resistance to oseltamivir have been increasing in recent years.

Methods for distinguishing viruses have been reported in a number of publications. For example, Marin M J et al. disclosed a method for distinguishing between human influenza virus and avian influenza virus. However, an effective method has not yet been developed which can determine whether or not patients suspected to have influenza infection would be infected with an oseltamivir-resistant virus.

PRIOR ART DOCUMENTS

Non-Patent Documents (Non-Patent Document 1) Marin M J et al. (Glyconanoparticles for the plasmonic detection and discrimination between human and avian influenza, Org Biomol Chem. 2013 Nov. 7; 11(41):7101-7).

DISCLOSURE

Technical Problem

It is an object of the present invention to provide a novel oseltamivir derivative compound, preferably oseltamivir hexylthiol or oseltamivir hexylamine, which can be used to detect oseltamivir-resistant virus.

Another object of the present invention is to provide a nanoparticle for detecting an oseltamivir-resistant virus, the nanoparticle having bound thereto the oseltamivir derivative compound, preferably oseltamivir hexylthiol or oseltamivir hexylamine.

Still another object of the present invention is to provide a method of detecting an oseltamivir-resistant virus by use of the nanoparticles.

Still another object of the present invention is to provide a kit for detecting an oseltamivir-resistant virus, the kit comprising the nanoparticle.

Yet another object of the present invention is to provide a method for treating influenza, the method comprising: detecting an oseltamivir-resistant virus by use of the nanoparticle; and administering a therapeutically effective amount of oseltamivir phosphate to a subject having no oseltamivir-resistant virus.

Technical Solution

The present invention provides an oseltamivir derivative compound represented by the following formula 1:

[Formula 1]

In the formula 1,
wherein $R_1$ is thiol or amine

Preferably, the oseltamivir derivative compound is an oseltamivir hexylthiol represented by the following formula 2 or an oseltamivir hexylamine represented by the following formula 3:

[Formula 2]

[Formula 3]

The present invention provides a nanoparticle for detecting an oseltamivir-resistant virus, the nanoparticle having bound thereto the oseltamivir derivative compound represented by formula 1. Preferably, the present invention provides a nanoparticle for detecting an oseltamivir-resistant virus, the nanoparticle having bound thereto the oseltamivir hexylthiol represented by formula 2 or the oseltamivir hexylamine represented by formula 3.

The nanoparticles of the present invention may be any nanoparticles which have a diameter of 1 to 100 nm and which can be observed visually or by an absorption/fluorescence spectrophotometer. For example, the nanoparticles may be gold nanoparticles, silver nanoparticles, fluorescent nanoparticles, fluorescent dyes, or the like. The gold nanoparticles and silver nanoparticles refer to particles having a diameter of 100 nm or less and various shapes (spherical, polygonal, etc.). The fluorescent nanoparticles are nanoparticles showing fluorescent properties and having a diameter of 100 nm or less. Even if the same material is used, the fluorescence wavelength thereof may vary depending on the particle size thereof, and thus fluorescence at various wavelengths can be obtained. Examples of the fluorescent nanoparticles include various nanoparticles which contain fluorescent dyes and quantum dots, and may be composed of a core having a size of about 2 to 10 nm and a shell made mainly of ZnS or the like. The II-VI or III-V group compounds forming the quantum dots may be selected, for example, from the group consisting of CdSe, CdSe/ZnS, CdTe/CdS, CdTe/CdTe, ZnSe/ZnS, ZnTe/ZnSe, PbSe, PbS InAs, InP, InGaP, InGaP/ZnS and HgTe (a single core or core/shell type). The Fluorescent dyes include, for example, fluorescent organic molecules (e.g., pyrene or its derivatives), cyanine (Cy) series, Alexa Fluor series, BODIPY series, DY series, rhodamine or its derivatives, fluorescein or its derivatives, coumarin or its derivatives, an acridine homodimer or its derivatives, Acridine Orange or its derivatives, 7-aminoactinomycin D (7-AAD) or its derivatives, actinomycin D or its derivatives, 9-amino-6-chloro-2-methoxyacridine (ACMA) or its derivatives, DAPI or its derivatives, dihydroethidium or its derivatives, ethidium bromide or its derivatives, ethidium homodimer-1 (EthD-1) or its derivatives, ethidium homodimer-2 (EthD-2) or its derivatives, ethidium monoazide or its derivatives, hexidium iodide or its derivatives, bisbenzimide (Hoechst 33258) or its derivatives, Hoechst 33342 or its derivatives, Hoechst 34580 or its derivatives, hydroxystilbamidine or its derivatives, LDS 751 or its derivatives, propidium iodide (PI) or its derivatives, calcein or its derivatives, Oregon Green or its derivatives, Magnesium Green or its derivatives, Calcium Green or its derivatives, JOE or its derivatives, tetramethylrhodamine or its derivatives, TRITC or its derivatives, TAMRA or its derivatives, pyronin Y or its derivatives, Lissamine or its derivatives, ROX or its derivatives, Calcium Crimson or its derivatives, Texas Red or its derivatives, Nile Red or its derivatives, thiadicarbocyanine or its derivatives, dansylamide or its derivatives, Cascade Blue, DAPI (4',6-diamidino-2-phenylindole), FITC, Cy3, Cy5, Cy5.5, Cy7 and the like. However, the kind of nanoparticle is not limited thereto. Each type of nanoparticle can be synthesized by a known method.

In one embodiment of the present invention, the nanoparticle may be a gold nanoparticle, but is not limited thereto.

It is known that oseltamivir-resistant influenza viruses generally have the H275Y mutation. In the art, H275Y can also be expressed as H274Y, and the H274Y mutation and the H275Y mutation are considered substantially the same. In the specification, the H275Y mutation has the same meaning as the H274Y mutation. Oseltamivir binds to influenza virus so as to reduce the neuraminidase (NA) activity, thereby killing the virus. When the H275Y mutation occurs, oseltamivir hardly binds to the virus.

The oseltamivir hexylamine or oseltamivir hexylthiol bound to the nanoparticle of the present invention binds to a virus showing oseltamivir resistance to due to the H275Y mutation, with about 1000-fold stronger affinity than to an oseltamivir sensitive virus. A detection method using a compound that binds to oseltamivir-sensitive viruses without binding to oseltamivir-resistant viruses was reported in the prior art. However, this method can merely detect the presence of an oseltamivir-resistant virus in a sample, and has a disadvantage in that it cannot distinguish the presence of an oseltamivir-resistant virus in a sample from the presence of pathogens other than influenza virus or the presence of influenza viruses of other serotypes or mutations or the absence of pathogens. Thus, this method has a disadvantage in that it is required to further perform a step of confirming the presence of an oseltamivir-resistant virus in a sample by use of other means such as specific antibodies, genetic assays or the like. However, the use of the present invention makes it possible to immediately detect the presence of an oseltamivir-resistant virus, indicating that the present invention makes it possible to detect an oseltamivir-resistant virus in a more accurate and convenient way compared to conventional methods.

The present invention also provides a method of detecting an oseltamivir-resistant virus by use of the nanoparticle.

Whether the nanoparticle of the present invention would bind to a virus can be confirmed by visual color comparison (colorimetry) or absorbance measurement. A person skilled in the art can easily distinguish between the presence and absence of an oseltamivir-resistant influenza virus in a sample, even though the results can vary depending on the kind and concentration of nanoparticle used and the amount of virus contained in the sample. For example, as shown in the right upper portion of FIG. 5, when an oseltamivir-resistant influenza virus was treated with the nanoparticle of the present invention, the color became more intense (due to increased binding between the virus and the nanoparticle) as the concentration of the nanoparticle used in the treatment increased. However, it can be seen that when an oseltamivir-sensitive influenza virus is treated with the nanoparticle of the present invention, a light color appears even when the concentration of the nanoparticle used in the treatment increases.

In one embodiment, the method of the present invention comprises the steps of: 1) contacting a sample isolated from a subject with a nanoparticle having bound thereto the oseltamivir hexylthiol represented by formula 2 or the oseltamivir hexylamine represented by formula 3; and 2) determining that an oseltamivir-resistant influenza virus is present in the sample, when the sample shows the same color as a color appearing when the nanoparticle was brought into contact with another sample in which the oseltamivir-resistant influenza virus is present.

In the method, the term "same color" means a color which can be regarded as substantially the same even if there are slight differences in reaction conditions, the chroma, brightness or hue of the sample, and the like.

In another embodiment, the method of the present invention comprises the steps of: 1) contacting a sample isolated from a subject with a nanoparticle having bound thereto the oseltamivir hexylthiol represented by formula 2 or the oseltamivir hexylamine represented by formula 3; and 2) determining that an oseltamivir-resistant influenza virus is present in the sample, when the sample shows a color different from a color appearing when the nanoparticle was brought into contact with another sample in which the oseltamivir-resistant influenza virus is not present.

Examples of the subject include humans or other animals, for example, birds or mammals.

The sample may be whole blood, serum, plasma, blood cells, endothelial cells, biopsy tissue, lymphatic fluid, ascitic fluid, interstitial fluid, bone marrow, cerebrospinal fluid (CSF), semen, saliva, mucus, sputum, sweat or urine.

The present invention also provides a kit for detecting an oseltamivir-resistant influenza virus, the kit comprising the nanoparticle. The kit of the present invention may further comprise other items necessary for detection and instructions for use.

The detection kit according to the present invention can be embodied in various forms. For example, it can be embodied in the form of a detection solution kit, a rapid kit (a kit making it possible to rapidly check the results due to movement of a sample on the kit after a small amount of the sample is dropped onto the kit using a lap-on-a-chip) or a paper stick.

In one embodiment, the detection kit according to the present invention may be a rapid diagnostic kit which is used as a diagnostic strip.

For example, the detection kit according to the present invention may comprise a sample pad, a conjugate pad, a nitrocellulose membrane and an adsorption pad, wherein oseltamivir hexylthiol-gold nanoparticles or oseltamivir hexylamine-gold nanoparticles are loaded on the conjugate pad, when a sample is moved through the sample pad, the oseltamivir hexylthiol-gold nanoparticles or oseltamivir hexylamine-gold nanoparticles loaded on the conjugate pad are moved to the nitrocellulose membrane and the adsorption pad together with the sample, and the nitrocellulose membrane has a control line and a test line, which are isolated from each other, wherein the control line has immobilized thereon an oseltamivir-resistant influenza virus containing H275Y mutation or the neuraminidase of the oseltamivir-resistant influenza virus containing H275Y mutation, and the test line has immobilized thereon the oseltamivir hexylthiol represented by formula 2 or the oseltamivir hexylamine represented by formula 3.

The present invention also provides a method of detecting an oseltamivir-resistant influenza virus by use of the detection kit.

In one embodiment, the detection method may comprise the steps of:

1) adding a sample to the conjugate pad of the detection kit and moving the sample; and 2) checking a change in the color of the control line and test line of the nitrocellulose membrane of the detection kit.

In the method of the present invention, when an oseltamivir-resistant influenza virus is not present in the sample, a color change appears only in the control line, but when the oseltamivir-resistant influenza virus is present in the sample, a color change appears in both the control line and the test line.

In the method of the present invention, the extent of the color change of the test line is large, it can be determined that the amount of oseltamivir-resistant influenza virus contained in the sample is large.

The present invention also provides a method for treating influenza, comprising the steps of:

treating a sample, obtained from a subject, with a nanoparticle for detecting an oseltamivir-resistant influenza virus, which has bound thereto the oseltamivir derivative compound represented by formula 1;

confirming whether or not an oseltamivir-resistant influenza virus comprising H275Y mutation is present in the sample; and administering a therapeutically effective amount of oseltamivir phosphate to the subject when the oseltamivir-resistant influenza virus is not detected in the sample or when the sample contains a very small amount of the oseltamivir-resistant influenza virus.

As used herein, the expression "when the oseltamivir-resistant influenza virus is not detected in the sample or when the sample contains a very small amount of the oseltamivir-resistant influenza virus" means a state in which the oseltamivir-resistant influenza virus is absent in the sample or the sample contains a very small amount of the oseltamivir-resistant influenza virus such that oseltamivir phosphate can exhibit a therapeutic effect in the subject.

As used herein, the term "therapeutically effective amount" means a reasonable oseltamivir phosphate dose applicable to any medical treatment, which is the amount of therapeutic agent which is statistically associated with a specific therapeutic effect when administered to a target population.

The detection kit of the present invention, the detection method using the same, and the treatment method using the same are not limited to the above-described exemplary embodiments.

In the case of conventional developed methods, the distribution and use of specific antibodies are limited due to their susceptibility to heat and pH, and genetic assays require detection instruments. However, the present invention has advantages in that the compound according to the present invention may be used even in high-temperature areas, can be stored for a long period of time, and can be commercialized in various forms.

Advantageous Effects

The oseltamivir analogue according to the present invention or a nanoparticle having bound thereto the analogue binds strongly to an oseltamivir-resistant influenza virus, and thus can be used to visually detect the oseltamivir-resistant influenza virus in a rapid and convenient manner. Therefore, the present invention can be advantageously used for quickly establishing a treatment plan for a patient infected with influenza virus.

FIG. 5 is a graph showing the results obtained by treating each of oseltamivir-sensitive virus and oseltamivir-resistant virus with oseltamivir hexylthiol-bound nanoparticles and measuring absorbance.

FIG. 6 is a schematic view showing the configuration of a rapid kit for detection of antiviral agent-resistant virus, prepared using oseltamivir analogue-gold nanoparticles of the present invention.

FIG. 7 shows the results of detecting antiviral agent-sensitive/resistant virus on a diagnostic rapid kit strip of the present invention.

MODE FOR INVENTION

Hereinafter, preferred examples of the present invention will be described in order to facilitate understanding of the present invention. However, these examples are provided only for the purpose of facilitating understanding of the present invention, and the scope of the present invention is not limited by these examples.

Example 1: Preparation of Nanoparticles

1-1: Synthesis of Oseltamivir Hexylthiol

Oseltamivir hexylthiol was synthesized according to the following scheme. In the following description, the numbers in the parentheses after the compound names refer to the numbers shown at the bottom of the compound formulas in the following scheme.

-continued

Synthesis of S-6-hydroxyhexyl Ethanethioate (2)

At room temperature, potassium ethanethioate (6.31 g, 55.2 mmol) was added slowly dropwise to a solution of 1-bromohexanol (1) (5.00 g, 27.6 mmol) in DMF (50 mL) while the solution was stirred. The reaction mixture as stirred for 12 hours, and then diluted with distilled water (30 mL). The mixture was extracted with $Et_2O$ (3×30 mL), and the organic layers were combined, dried with anhydrous $MgSO_4$, filtered, and then concentrated. The concentrate was separated by column chromatography (hexane: EtOAc=2:1-1:1) to obtain compound 2 (4.20 g, 86%) as a light yellow liquid.

Synthesis of (3R,5S)-ethyl-4-acetamido-5-(tert-butoxycarbonylamino)-3-(pentan-3-yloxy)cyclohex-1-enecarboxylate (4)

At room temperature, di-tert-butyl dicarbonate (7.84 mL, 34.1 mmol) and triethylamine (6.80 mL, 48.8 mmol) were added dropwise to a solution of oseltamivir phosphate salt (3) (10.0 g, 24.4 mmol) in MeOH (50 mL) while the solution was stirred. The reaction mixture was stirred at room temperature for 12 hours. Distilled water (100 mL) was added to the mixture which was then stirred for 1 hour. Next, the produced white solid was filtered and washed with distilled water. The filtrate was dried in a vacuum oven to obtain compound 4 (5.71 g, 56%) as a white solid.

Synthesis of (3R,5S)-4-acetamido-5-(tert-butoxycarbonylamino)-3-(pentan-3-yloxy)cyclohex-1-enecarboxylic Acid (5)

At room temperature, NaOH (663 mg, 16.6 mmol) was added to a solution of compound 4 (5.70 g, 13.8 mmol) in THF/H$_2$O (10:1, v/v, 30 mL) while the solution was stirred. The reaction mixture was stirred for 24 hours, and then concentrated to remove the reaction solvent. The concentrate was diluted with distilled water (20 mL), and the reactor was cooled to 0° C. The mixture was acidified to a pH 5 by addition of 1M HCl aqueous solution, and then stirred for 1 hour. The produced white solid was filtered and washed with distilled water. The filtrate was dried in a vacuum oven to obtain compound 5 (4.0 g, 75%) as a white solid.

Synthesis of (3R,5S)-6-(acetylthio)hexyl-4-acetamido-5-(tert-butoxycarbonylamino)-3-(pentan-3-yloxy)cyclohex-1-enecarboxylate (6)

At room temperature, compound 2 (2.20 g, 12.5 mmol), 1-ethyl-3-(3-dimethyl-aminopropyl)carbodiimide hydrochloride (2.79 g, 14.6 mmol), 4-(dimethylamino)pyridine (1.52 g, 12.5 mmol) and triethylamine (2.90 mL, 20.8 mmol) were sequentially added to a solution of compound 5 (4.00 g, 10.4 mmol) in CH$_2$Cl$_2$ (30 mL) while the solution was stirred. After stirring at room temperature for 24 hours, distilled water was added to the reaction mixture to stop the reaction. The mixture was extracted with CH$_2$Cl$_2$ (3×30 mL), and the organic layers were combined, dried with anhydrous Na$_2$SO$_4$, filtered, and then concentrated. The concentrate was separated by column chromatography (hexane:EtOAc=2:1-1:1) to obtain compound 6 (3.51 g, 62%) as a colorless liquid.

Synthesis of Oseltamivir Hexylthiol (7)

At room temperature, concentrated hydrochloric acid (2.15 mL, 25.8 mmol) was added slowly dropwise to a solution of compound 6 (3.50 g, 6.45 mmol) in MeOH (30 mL) while the solution was stirred. The reactor was heated at 50° C. for 72 hours. The reaction mixture was cooled to room temperature, and then concentrated to remove the reaction solvent. The concentrate was diluted with MeOH (5 mL), and Et$_2$O was added slowly dropwise thereto with stirring. The produced white solid was filtered and washed with Et$_2$O. The filtrate was dried on a vacuum oven to obtain compound 7 (oseltamivir hexylthiol) (560 mg, 20%) as a white solid.

The oseltamivir hexylthiol is represented by the following formula 2:

[Formula 2]

1-2: Synthesis of Oseltamivir Hexylamine

Oseltamivir hexylamine was synthesized according to the following scheme. In the following description, the numbers in the parentheses after the compound names refer to the numbers shown at the bottom of the compound formulas in the following scheme.

Synthesis of tert-butyl 6-hydroxyhexylcarbamate (9)

At room temperature, di-tert-butyl dicarbonate (6.47 mL, 28.2 mmol) was added dropwise to a solution of compound 8 (3.00 g, 25.6 mmol) in MeOH (30 mL) while the solution was stirred. The reaction mixture was stirred at room temperature for 6 hours, and then concentrated. The concentrate was separated by column chromatography (hexane: EtOAc=2:1-1:1) to obtain compound 9 (4.10 g, 74%) as a light yellow liquid.

Synthesis of (3R,5S)-6-(tert-butoxycarbonylamino)hexyl-4-acetamido-5-(tert-butoxycarbonylamino)-3-(pentan-3-yloxy)cyclohex-1-enecarboxylate (10)

At room temperature, compound 9 (2.18 g, 10.0 mmol), 1-ethyl-3-(3-dimethyl-aminopropyl)carbodiimide hydrochloride (2.44 g, 12.7 mmol), 4-(dimethylamino)pyridine (1.33 g, 10.9 mmol) and triethylamine (2.54 mL, 18.2 mmol) were sequentially added to a solution of compound 5 (3.50 g, 9.10 mmol) in DMF (20 mL). After stirring at room temperature for 24 hours, distilled water was added to the reaction mixture to stop the reaction. The mixture was extracted with EtOAc (3×20 mL), and the organic layers were combined, dried with anhydrous $Na_2SO_4$, filtered, and then concentrated. The concentrate was separated by column chromatography (hexane:EtOAc=2:1-1:1) to obtain compound 10 (2.41 g, 45%) as a yellow liquid.

Synthesis of Oseltamivir Hexylamine (11)

At room temperature, concentrated hydrochloric acid (1.75 mL, 21.0 mmol) was added slowly dropwise to a solution of compound 10 (2.45 g, 4.20 mmol) in MeOH (20 mL) while the solution was stirred. After stirring at room temperature for 24 hours, the reaction mixture was concentrated to remove the reaction solvent. The concentrate was diluted with MeOH (5 mL), and $Et_2O$ was added slowly dropwise thereto with stirring. The produced white solid was filtered and washed with $Et_2O$. The filtrate was dried in a vacuum oven to obtain compound 11 (oseltamivir hexylamine) (1.15 g, 65%) as a white solid.

The oseltamivir hexylamine is represented by the following formula 3:

[Formula 3]

1-3: Synthesis of Gold Nanoparticles 1 wt % $HAuCl_4$ solution (1 mL) was added to 100 mL of distilled water, and the solution was vigorously stirred at 95° C. In this state, 1 wt % of sodium citrate (5 mL) was immediately added slowly to the solution, and was reacted under the same conditions for 30 minutes.

1-4: Nanoparticle-Oseltamivir Analogue Binding 5 mL of the gold nanoparticle solution synthesized in 1-3 above was centrifuged at 15000 rpm for 10 minutes to remove an excess of sodium citrate. The supernatant was discarded, and the residue was resuspended in 1 mL of distilled water, and then centrifuged at 15000 rpm for 10 minutes. This process was repeated twice more. In the last step, the supernatant was discarded, and 1 mL of the oseltamivir hexylamine or oseltamivir hexylthiol (6 mg/mL) suspended in distilled water was added to the residue. Next, the solution was vortexed for more than 12 hours so that the oseltamivir hexylamine or oseltamivir hexylthiol was bound to the gold nanoparticles. Then, the solution was centrifuged at 15000 rpm for 20 minutes, and the supernatant was removed and the residue was resuspended in 100 μL of distilled water.

Example 2: Comparison of Neuraminidase Activities of Viruses 2-1: Comparison of the Effects of Oseltamivir Hexylthiol and Oseltamivir Hexylamine on Neuraminidase Activities of Viruses Using NA-Fluor™ Influenza Neurmaminidase Assay Kit (AB Applied biosystem, Prod No. 4457091), NA enzyme activities were measured.

Specifically, solution A was prepared by dissolving NA-Fluor (480 μL) in a working solution (5.52 mL) in the kit. A virus solution was prepared such that 100 or 1000 viruses would be contained in each well. As a wild type (antiviral agent-sensitive virus), pandemic H1N1 virus (A/04/2009/California) (pandemic H1N1) was used, and as a mutant type (antiviral agent-resistant virus), Influenza A/Korea/2785/2009 (H275Y mutation) was used. 19.3 mg of oseltamivir hexylamine or oseltamivir hexylthiol was prepared in 2 mL of distilled water (solution C). 50 μL of solution A was added to each well of a 96-well plate, and each virus sample solution was added to each well. 50 μL of solution C was added to each well at varying concentrations (only distilled water was added in a control group). Namely, solution A+each virus solution (wild type or mutant type)+solution C was added to each well. After 1 hour of incubation at 37° C., 50 μL of NA-Fluor stop buffer solution was added to each well. NA activity at the protein level was measured by measuring fluorescence at an excitation wavelength (EX) of 360 nm and an emission wavelength (EM) of 450 nm. Higher NA activity indicates higher fluorescence intensity.

Figure 1:
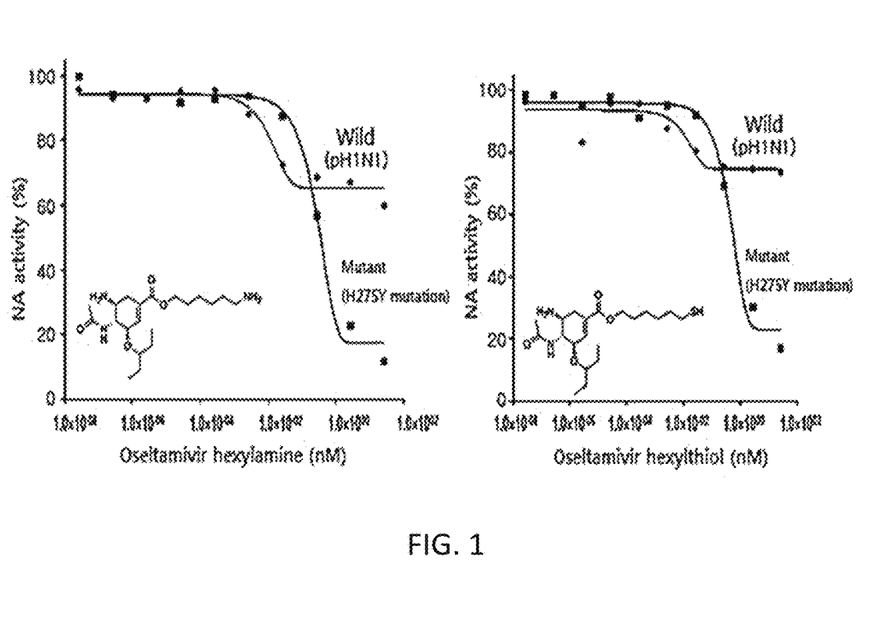
FIG. 1 shows the results of measuring the extent to which oseltamivir hexylamine and oseltamivir hexylthiol inhibited the neuraminidase activities of oseltamivir-sensitive virus and oseltamivir-resistant virus at the virus level.

The results of the measurement are shown in FIG. 1. From the left side (oseltamivir hexylamine) and right side (oseltamivir hexylthiol) of FIG. 1, it can be seen that high concentrations of oseltamivir hexylamine and oseltamivir hexylthiol inhibited the NA activity of the mutant-type virus (H275Y mutation) more significantly than the NA activity of the wild-type virus.

2-2: Measurement of Change in Absorbance after Treatment of Viral Neuraminidase Protein with Oseltamivir Analogue-Gold Nanoparticles Neuraminidase protein isolated from the wild-type or mutant-type virus was added to each well of a 96-well plate in an amount of 0.1 mg (100 μg)/well, and the oseltamivir hexylthiol-bound gold nanoparticles synthesized in Example 1-4 above were added to each well in an amount of 100 μL (1.22 mg in terms of gold ion concentration), after which the absorbance of each well was measured at a wavelength of 400 to 750 nm.

Figure 2:
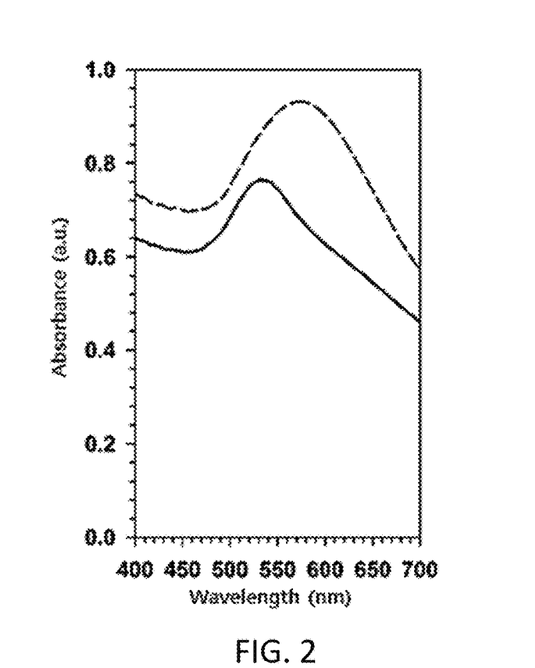
FIG. 2 is a graph showing the results obtained by treating each of oseltamivir-sensitive virus and oseltamivir-resistant virus with oseltamivir analogue-gold nanoparticles and measuring absorbance.

The results of the measurement are shown in FIG. 2. As can be seen in FIG. 2, the absorbance wavelength for the mutant type (dotted line) was longer than the absorbance wavelength for the wild type (full line), indicating that the oseltamivir hexylthiol-bound gold nanoparticles show different absorbance wavelengths for the neuraminidase proteins of the wild type and the mutant type.

Example 3: Analysis of the Binding Affinity of Oseltamivir Analogue for Oseltamivir-Resistant Virus The binding energy ($\Delta G_{bind}$) of the oseltamivir hexylthiol of the present invention for the neuraminidase site of oseltamivir-sensitive virus (wild type) and oseltamivir-resistant virus (mutant type) was calculated.

Figure 3:
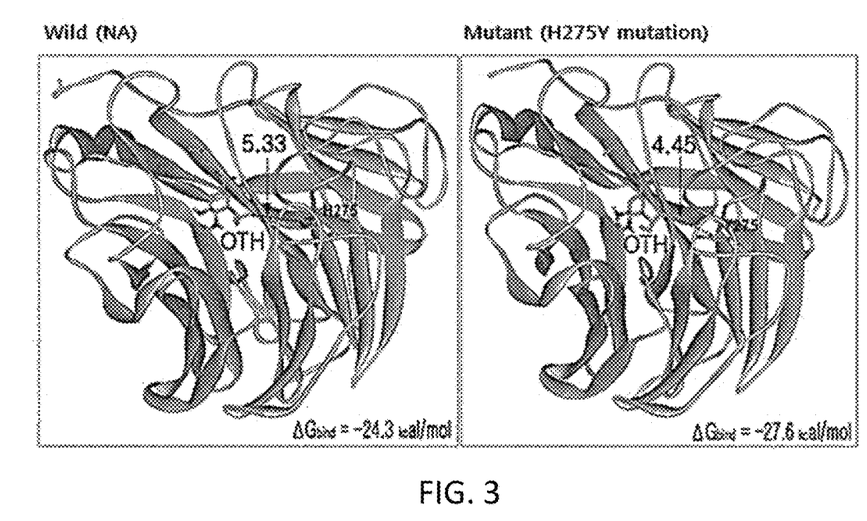
FIG. 3 is a schematic view showing the patterns of binding of the oseltamivir hexylamine and oseltamivir hexylthiol of the present invention to oseltamivir-sensitive virus and oseltamivir-resistant virus. The oseltamivir hexylthiol whose formula is shown in the left lower portion of FIG. 3 showed about 250-fold higher $\Delta G_{bind}$ to oseltamivir-resistant virus.

As a result, it was shown that the binding energy of the oseltamivir hexylthiol for the wild type was −24.33 kcal/mol, but the binding energy of the oseltamivir hexylthiol for the mutant type was −27.62 kcal/mol (see FIG. 3). This suggests that the oseltamivir hexylthiol binds to the mutant type with about 250-fold higher affinity than to the wild type.

Example 4: Development of Antiviral Agent-Resistant Virus Detection System Using Oseltamivir Analogue-Gold Nanoparticles and Evaluation of Performance Thereof The oseltamivir analogue-gold nanoparticles of the present invention bind to oseltamivir-resistant virus with high affinity. Thus, when the nanoparticles are added to oseltamivir-resistant virus, a color change occurs so that the virus can be visually detected.

The virus was prepared to contain 0, 10, 100 or 1000 viruses per each well of a 96-well plate. As a wild type (antiviral agent-sensitive virus), pandemic H1N1 virus (A/04/2009/California) (pandemic H1N1) was used, and as a mutant type (antiviral agent-resistant virus), Influenza A/Korea/2785/2009 (H275Y mutation) was used. 100 μL (1.22 mg in terms of gold ion concentration) of the oseltamivir hexylthiol-gold nanoparticles synthesized in Example 1 were added to each well, after which the absorbance of each well was measured at a wavelength of 400 to 750 nm to detect antiviral agent-sensitive/resistant virus by a color change.

Figure 4:
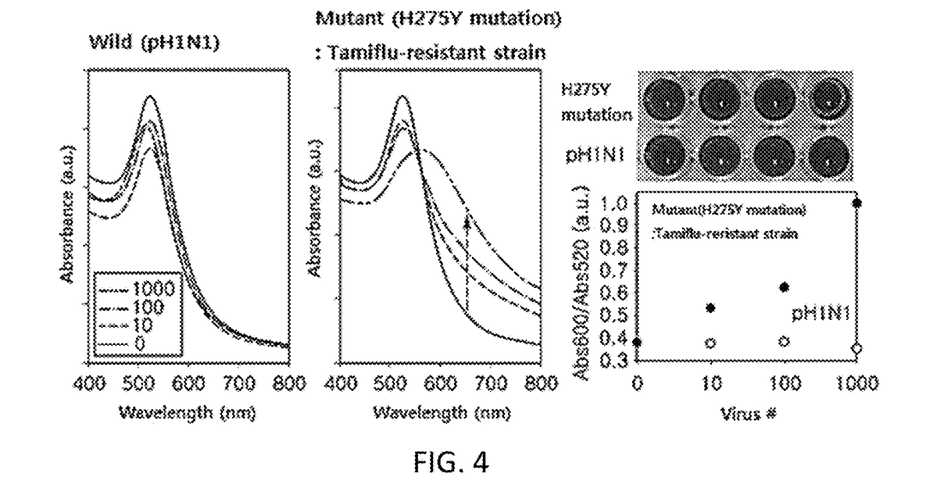
FIG. 4 shows absorbance graphs (left), visual observation of a color difference (right upper) and a graph showing the color difference (right bottom), which resulted when oseltamivir hexylthiol-bound gold nanoparticles were allowed to react with each of oseltamivir-sensitive virus and oseltamivir-resistant virus.

The results of the measurement are shown in FIG. 4. As can be seen in the left side of FIG. 4, even when the number of the oseltamivir-sensitive viruses (wild type) increased, there was little or no change in the absorbance wavelength of the oseltamivir hexylthiol-gold nanoparticles, but as the number of the oseltamivir-resistant viruses (mutant type) increased, the absorbance wavelength of the oseltamivir hexylthiol-gold nanoparticles was shifted. This is a phenomenon caused by a color change from the original color due to an increase in the number of oseltamivir hexylthiol-gold nanoparticles bound to the oseltamivir-resistant viruses, and can also be visually detected (the right upper portion of FIG. 4). This phenomenon is graphically shown in the right bottom side of FIG. 4. From the graph, it can be clearly seen that the absorbance wavelength was shifted.

Figure 5:
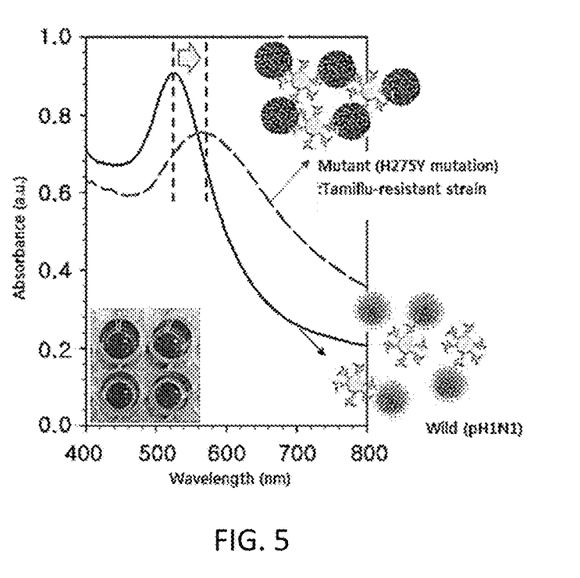

In addition, FIG. 5 shows the results of measuring absorbance in the case in which 1000 wild type viruses and mutant type viruses were added to each well in the above experiment. From the left bottom of FIG. 5, it can be visually seen that a color change appeared (the color in FIG. 5 was different from that in FIG. 4 because the background light for the plate was brighter)

Figure 6:
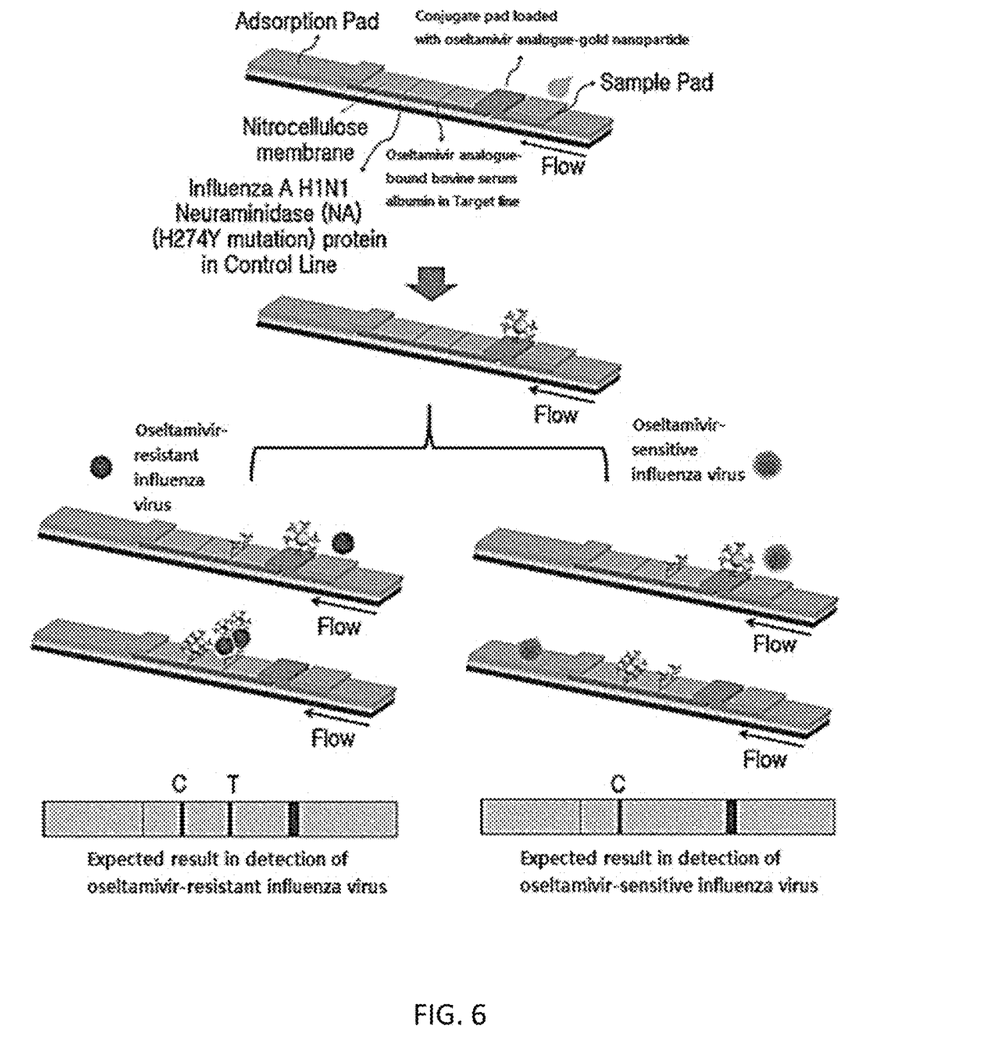

Example 5: Development of Rapid Diagnostic Kit for Antiviral Agent-Resistant Virus Detection Based on Oseltamivir Analogue-Gold Nanoparticles Using the oseltamivir analogue-gold nanoparticles prepared in Example 1, a rapid kit for oseltamivir-resistant influenza virus detection was prepared (FIG. 6). Specifically, oseltamivir-bound bovine serum albumin (BSA) (test line) and 3.3 mg/mL of the neuraminidase protein of an oseltamivir-resistant influenza virus comprising H275Y mutation (control line) were dropped onto a nitrocellulose membrane, thereby preparing a strip having a size of 4 mm×50 mm. Next, oseltamivir hexylthiol-gold nanoparticles were dispensed onto the conjugate pad of the strip, and then dried. The rapid kit of the present invention is configured such that when a sample is moved through a sample pad, the oseltamivir hexylthiol-gold nanoparticles on the conjugate pad are moved together with the sample and adsorbed onto an adsorption pad through the nitrocellulose membrane.

Figure 7:
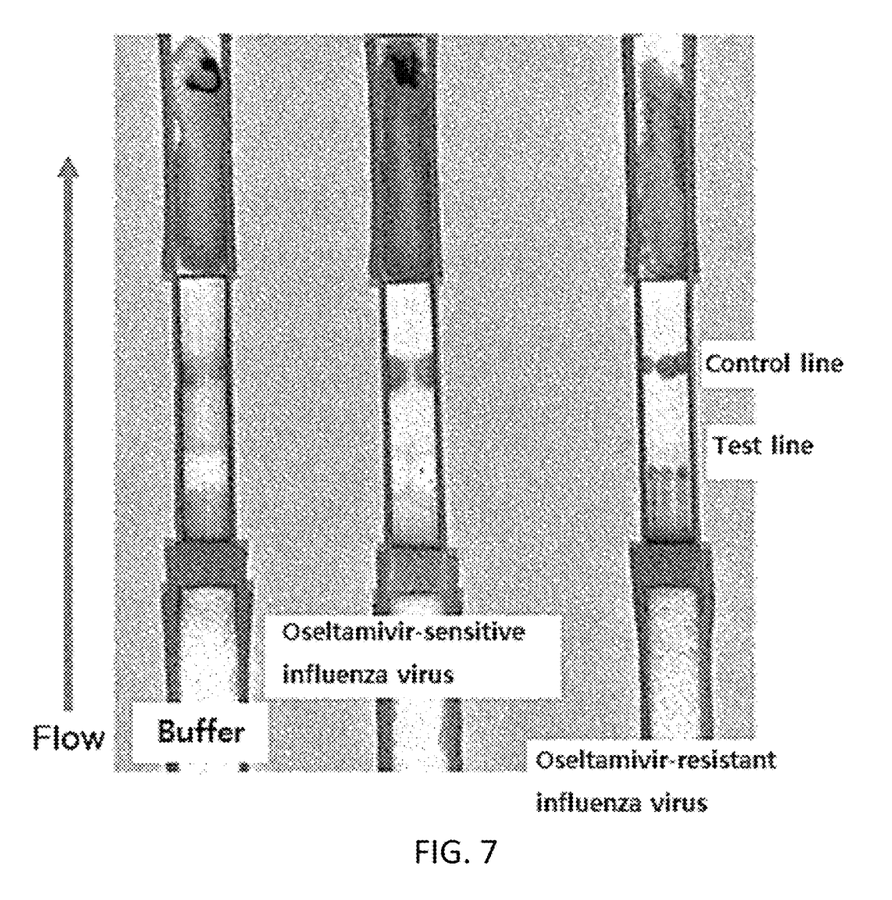

Example 6: Detection of Oseltamivir-Resistant Influenza Virus by Use of Rapid Diagnostic Kit Based on Oseltamivir Analogue-Gold Nanoparticles The ability of the rapid kit (prepared in Example 5) to detect oseltamivir-sensitive/resistant influenza virus was evaluated. When a buffer sample containing no influenza virus was added to the rapid kit, a line appeared only in the control line, and did not appear in the test line. Furthermore, when a buffer containing oseltamivir-sensitive virus (wild type) was added to the rapid kit, a line also appeared only in the control line. However, when a buffer containing oseltamivir-resistant virus (mutant type) was added to the rapid kit, a line appeared in both the control line and the test line (FIG. 7). Such results suggest that oseltamivir-resistant influenza virus can be efficiently detected using a rapid kit comprising the oseltamivir analogue-gold nanoparticles of the present invention.

The invention claimed is:

1. A compound of an oseltamivir hexylthiol represented by the following formula 2 or an oseltamivir hexylamine represented by the following formula 3:

(Formula 2)

(Formula 3)

2. A nanoparticle for detecting an oseltamivir-resistant influenza virus comprising H275Y mutation, the nanoparticle having bound thereto a compound of an oseltamivir hexylthiol represented by the following formula 2 or an oseltamivir hexylamine represented by the following formula 3:

(Formula 2)

(Formula 3)

3. The nanoparticle of claim 2, wherein the nanoparticle is a gold nanoparticle, a silver nanoparticle, or a fluorescent nanoparticle.

4. The nanoparticle of claim 2, wherein the nanoparticle has a higher binding affinity for the oseltamivir-resistant influenza virus comprising H275Y mutation than for an oseltamivir-sensitive influenza virus.

5. A kit for detecting an oseltamivir-resistant influenza virus comprising H275Y mutation, the kit comprising the compound of claim 1.

6. A method for treating influenza, comprising:
   treating a sample obtained from a subject with the nanoparticle of claim 2;
   confirming whether or not an oseltamivir-resistant influenza virus comprising H275Y mutation is present in the sample; and
   administering a therapeutically effective amount of oseltamivir phosphate to the subject when the oseltamivir-resistant influenza virus is not detected in the sample or when the sample contains a very small amount of the oseltamivir-resistant influenza virus.

7. The method of claim 6, wherein the confirming is performed using colorimetry.

8. The method of claim 6, wherein the confirming is performed visually.

* * * * *